United States Patent [19]

Simon et al.

[11] Patent Number: 4,577,639

[45] Date of Patent: Mar. 25, 1986

[54] APPARATUS AND METHOD FOR AUTOMATIC LEAD SELECTION IN ELECTROCARDIOGRAPHY

[75] Inventors: Mark I. Simon, Chatsworth; Christopher G. Cotter, Van Nays; Carolyn Stein-Gelinas, Agoura, all of Calif.

[73] Assignee: Spacelabs, Inc., Chatsworth, Calif.

[21] Appl. No.: 669,290

[22] Filed: Nov. 8, 1984

[51] Int. Cl.⁴ .............................................. A61B 5/04
[52] U.S. Cl. ..................................... 128/709; 128/696
[58] Field of Search ................ 128/695, 696, 709, 710

[56] References Cited

U.S. PATENT DOCUMENTS

| | | |
|---|---|---|
| 3,513,833 | 5/1976 | Finch et al. .......................... 128/709 |
| 3,561,430 | 2/1971 | Filler, Jr. et al. .................... 128/661 |
| 3,602,215 | 8/1971 | Parnell ................................. 128/696 |
| 3,648,689 | 3/1972 | Dominy .............................. 128/709 |
| 3,911,905 | 10/1975 | Rossel ................................ 128/709 |
| 4,141,351 | 2/1979 | James et al. ......................... 128/709 |
| 4,299,234 | 11/1981 | Epstein et al. ...................... 128/698 |

Primary Examiner—William E. Kamm
Attorney, Agent, or Firm—Lawrence S. Levinson; Robert E. Lee, Jr.

[57] ABSTRACT

An ECG electrode impedance measuring approach is utilized which can determine, simultaneously, the condition of all electrodes in a three or five lead ECG monitoring configuration. A CPU automatically selects an ECG lead configuration in which all electrodes are attached to the patient and are below an impedance threshold. If the CPU cannot select a good ECG lead configuration, then the CPU signals a total lead failure. Electrode impedance is determined by passing a small DC current through each active electrode and the current is returned via the reference electrode. A comparator tests the resultant offset voltage induced between each active electrode and the reference. If the offset voltage exceeds a fixed threshold, then a flag is set and transferred to the CPU. The CPU can change the ECG lead configuration by issuing commands to an electrode lead switching network. The CPU software tests each lead configuration in a logical sequence to find one in which all the necessary electrodes are functional and a good quality ECG waveform can be processed and displayed. If a useable lead configuration cannot be found, then an alarm is activated to alert the operator to check all electrodes.

8 Claims, 4 Drawing Figures

APPARATUS AND METHOD FOR AUTOMATIC LEAD SELECTION IN ELECTROCARDIOGRAPHY

BACKGROUND OF THE INVENTION

This invention relates to electrocardiography (ECG) and more particularly to automatic sensing of ECG lead failure and automatic switching of the ECG lead configuration in response thereto.

In electrocardiography, a plurality of electrodes with attached leads (hereinafter leads) are applied to selected regions of a patient's body in order to sense electrical signals generated thereon in response to the patient's heart muscle activity. A number of standard lead configurations have come into common practice involving three, five and even twelve leads.

The opposite ends of the leads are coupled to an isolated ECG preprocessor including a lead switch where electrical signals are combined in a well known predetermined fashion depending on which lead configuration has been selected by the attending individual. The output signal resulting from this combination (after suitable filtering and amplification) is the patient's electrocardiogram or ECG signal.

In some known digital ECG monitors, the ECG signal is then digitized and the digitized waveform is processed further under the control of a microprocessor CPU, e.g., for heartbeat detection, heart rate calculation, arrhythmia detection and classification of the condition of the heart. In prior art monitors the CPU is capable of controlling the ECG lead switch to insure the right combination of lead signals in response to knowledge of the electrode lead configuration presently in place.

However, it is sometimes the case that one or more of the electrodes will become detached as a result of patient movement or were never properly attached in the first place. This will usually result in a distorted or a useless ECG signal with subsequent reduced or nonexistent ability to perform proper ECG analysis. It is highly desirable therefore to be able to automatically detect one or more lead failures and further to automatically switch when possible to an alternate lead configuration which reduces the effect of the lead failure and provides an acceptable ECG signal for processing until the problem can be corrected.

SUMMARY OF THE INVENTION

An object of the present invention is to provide an improved method and apparatus for ECG monitoring by providing automatic detection of ECG electrode/lead failures, and automatic reconfiguration of the combined electrode leads based on the above detection.

In an ECG monitor having a switch controlled ECG signal preprocessor for providing an ECG signal from one of a plurality of ECG lead configurations, means are provided for detecting and identifying one or more ECG lead failures. In response to the detection and identification of the lead failure processor means coupled to the switch controlled ECG signal preprocessor automatically changes the lead configuration to continue ECG monitoring when possible.

The detector means further comprises means for measuring the impedance of each of the active electrodes by passing a small dc current through the electrode and patient to ground through a preselected reference electrode. The voltage produced by the dc current is compared with a preselected threshold voltage to determine if the impedance of the electrode is too high.

Depending on the number and identity of the failed electrodes and the present lead configuration, automatic lead switching means determine which leads are to be switched to form a new combination. Both three and five lead configurations are accommodated when a five wire cable is used.

DETAILED DESCRIPTION OF THE DRAWINGS

Figure 1:
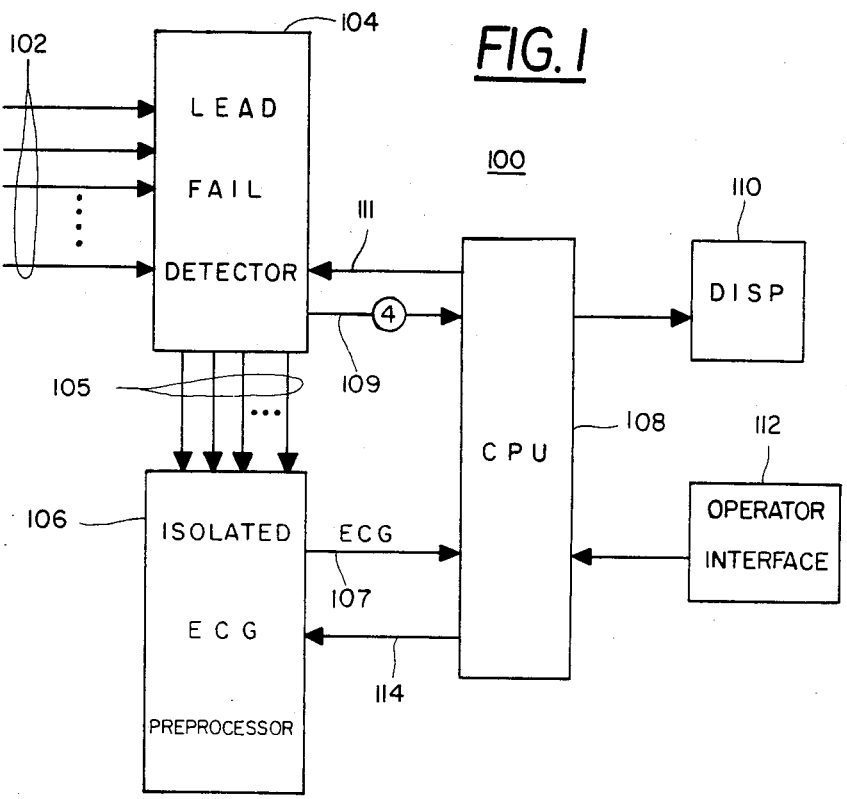
FIG. 1 is an overall block diagram of the improved ECG monitor of the present invention.

Referring now to FIG. 1, a simplified block diagram of an improved digital ECG monitor incorporating the present invention designated generally 100 is disclosed. Leads 102 from the electrodes placed on a patient are coupled to a lead fail detector means 104 for detecting when one or more leads are disconnected or improperly connected. The number of leads 102 can vary depending on the configuration selected with typical configurations employing three, five and sometimes twelve leads. More will be said about this later. The signals from the leads are transmitted from the lead fail circuit 104 over lines 105 to an isolated ECG preprocessor 106.

Preprocessor 106 accepts the ECG lead signals from lead fail circuit 104 and combines them in a well known manner in analog fashion in accordance with the lead configuration chosen. The combined output of the analog signal is digitized and provided as a digital ECG signal over line 107 to the CPU controller 108 for disposition for further programmed processing. The digitized ECG signals and other signals and information resulting from the processing are displayed on display 110.

The CPU accepts operator commands and inputs from a keyboard 112 or other input device. In one embodiment the operator interface and keyboard can be combined using touch screen technology.

Figure 2:
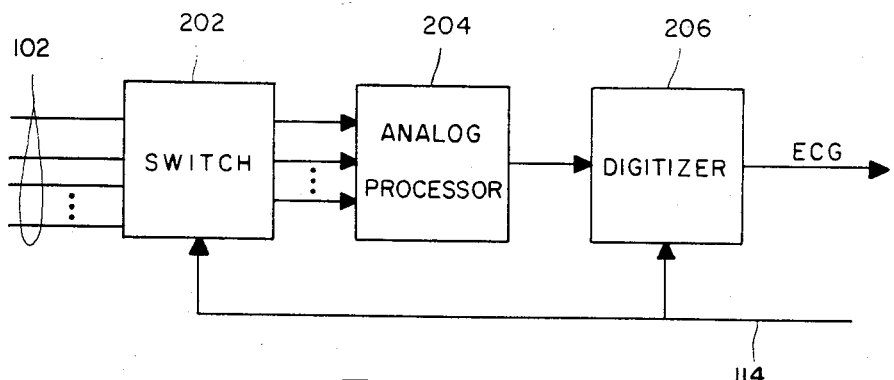
FIG. 2 is a more detailed block diagram of the isolated ECG preprocessor portion of the monitor of FIG. 1.

Referring now to FIG. 2, the isolated ECG preprocessor 106 is shown further in more detail comprising a digitally controlled switch 202 controlled by a multi-bit command signal from the CPU 108 over bus 114, the command being appropriate to the electrode configuration used with the patient. The electrode signals are provided in the proper arrangement associated with the selected electrode configuration by the switch 202 to the analog processor 204 comprised of differential amplifiers etc. The output is provided to a digitized portion 206 made up of A/D converters and sample and hold circuits. The necessary clock and command signals are provided by CPU 108 over bus 114.

The CPU may comprise one or more microprocessors wherein a first microprocessor such as an SN32000 is located in the same module as the preprocessor and controls the lead switching, signal processing, beat detection and classification. A second microprocessor, such as an Intel 80186, receives the processed ECG signal over a serial data bus for display and distribution over network. Alternatively, all of the above can be accomplished by a single CPU such as is depicted in FIG. 1 for clarity.

Table 1 is a table showing the names of various well known leads in the right most column; the lead configuration nomenclature in the left most column; and the appropriate operation to be performed on the electrode signals by the switching and analog circuits 202 and 204 for each of the configurations in the center column. For example, when three bipolar limb leads (Einthoven leads) are used to record an ECG, the leads are placed on the left arm (LA), right arm (RA) and left leg (LL). In the three lead configuration known as configuration I the LL lead is a reference lead (i.e., it is connected to electrical ground), and the RA signal is subtracted from the LA signal by the switching and analog circuits 202 and 204. As Table 1 shows, in configuration II, RA is subtracted from LL and LA is the reference. Configuration III is also shown with RA as the reference. The three lead configurations I, II, and III can also be used with a five lead cable. The remaining two leads are attached but not combined to provide an ECG output.

TABLE 1
Definition of Lead Configurations

| Lead Nomenclature | Definition | Name of Lead |
|---|---|---|
| I | I = LA − RA | Bipolar limb leads (Einthoven) |
| II | II = LL − RA |  |
| III | III = LL − LA |  |
| AVR | aVR = RA − 0.5 (LA + LL) | Augmented leads (Goldberg) |
| AVL | aVL = LA − 0.5 (LL + RA) |  |
| AVF | aVF = LL − 0.5 (LA + RA) |  |
| $V_1$ | $V_1 = V − 0.333 (LA + RA + LL)$ | Unipolar chest leads (Wilson) |
| $V_2$ | $V_2 = V − 0.333 (LA + RA + LL)$ |  |
| $V_3$ | $V_3 = V − 0.333 (LA + RA + LL)$ |  |
| $V_4$ | $V_4 = V − 0.333 (LA + RA + LL)$ |  |
| $V_5$ | $V_5 = V − 0.333 (LA + RA + LL)$ |  |
| $V_6$ | $V_6 = V − 0.333 (LA + RA + LL)$ |  |

When a five electrode configuration is used there are five body locations: RA, LA and LL, as above, along with right leg (RL) and chest. The list of five electrode configurations using Wilson electrodes are provided in Table 1 as AVR, AVL, AVF and $V_1$ through $V_6$. On all five electrode configurations listed the RL electrode is the reference electrode; and V is the chest electrode. The numbers $V_1$–$V_6$ refer to the particular location on the chest where the V electrode is placed. Table 1 shows how the various electrode signals are to be combined by the switching and analog circuitry 202 and 204 for each of the five electrode configurations.

The CPU 108 is informed of which lead configuration is being used by either the operator or automatically by the monitor. The CPU via bus 114 controls the switch 202 to effect the proper configuration of signals for input to the analog circuit 204 which operates in accordance with the algebraic equations shown in the center column of Table 1.

However, it is sometimes the case that one or more leads are unattached or poorly attached to the patient causing the formation of an unacceptable ECG signal and subsequent poor processing. This situation may go undetected for a long period of time during which period valuable ECG information is lost. When the error is detected it is usually corrected manually.

In the present invention, an improved ECG monitor is provided by adding means for the automatic detection and identification of lead failures and automatic lead switching when possible in response to the detection of lead failures.

Figure 3:
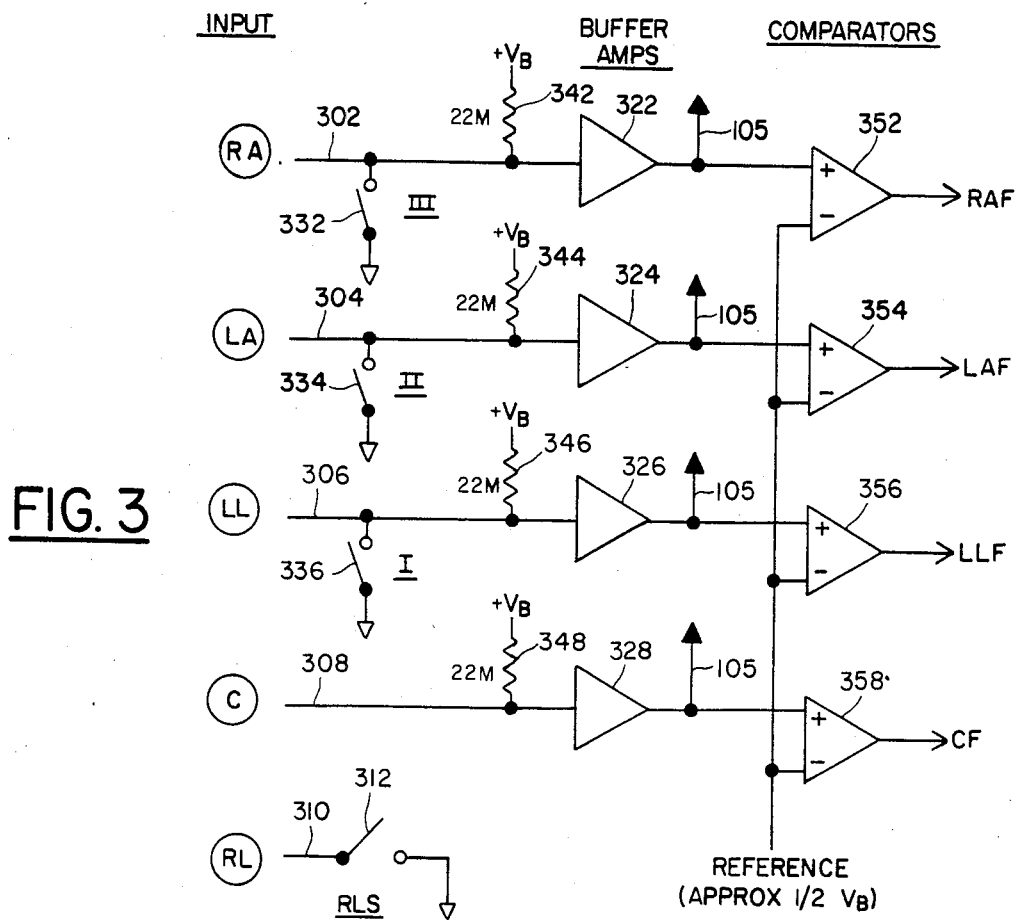
FIG. 3 is a schematic drawing of the lead fail detector portion of FIG. 1.

Referring now to FIG. 3, a more detailed description of the lead fail detection circuit 104 is provided. A five lead configuration is shown. The lead even numbers 302 through 310 are coupled at one end to electrodes attached to specific locations on the patient. The leads 302 through 310 correspond to leads RA; LA; LL; V; and RL, respectively. These were described above in connection with Table 1. As noted before RL is always the reference lead in a five lead configuration and is shown in FIG. 3 coupled to ground through switch 312. When RL is used as the reference switch 312 is closed. Each of the leads even numbers 302 through 310 are coupled at their other end to buffer amplifiers even numbers 322 through 328, respectively. In the preferred embodiment, Signetic amplifiers Model No. NE 5514, are used. Each of the leads 302 through 308 on the buffer amplifier input side are coupled to electrical ground through switches even numbers 332 through 336. Lead 308 is not coupled to ground. The switches even numbers 332 through 336 and 312 are normally part of the switch 202 of ECG preprocessor 106. Each of the leads 302 through 308 on the buffer amplifier input side are connected to a voltage source $V_B$ through 22 megohm resisters even numbers 342 through 348, respectively.

The outputs of buffer amplifiers 322 through 328 are coupled to the positive terminal of comparators even numbers 352 through 358, respectively, and to the isolated ECG preprocessor 106 via lines 105. The negative terminal of the comparators are each coupled together to a reference voltage, which in the preferred embodiment is approximately $\frac{1}{2}V_B$. Suitable comparators are made by National Semiconducer, Model No. LM339.

Using first a five electrode configuration as an example, the circuit 102 works in the following way: switch 312 is closed and the voltage $V_B$, typically 0.7 volts, provides a small dc current through each 22M resister; through each lead and associated electrode; through the patient; and finally through the lead RL and closed switch 312 to ground. This produces a dc voltage in each lead which is proportional to the impedance of the associated electrode. With this arrangement if the electrical impedance of the electrode/lead combination exceeds 22 megohms the voltage at the positive terminal of the comparator will exceed the threshold voltage at the negative terminal and the comparator will provide a high level signal indicating a lead failure. A four bit bus 109 transits the status of the comparators in parallel to the CPU 108.

If a three lead configuration is used, such as configurations I, II, III, then it is necessary to provide one of leads 302, 304 or 306 as a reference. For this reason these leads are coupled to ground through switches 332, 334 and 336, respectively. The switches are digitally controlled by CPU 108 via line 111.

Hence, the detector circuit 104 provides a means for determining the status of each of the ECG leads and a means for identifying those leads which fail.

Figure 4:
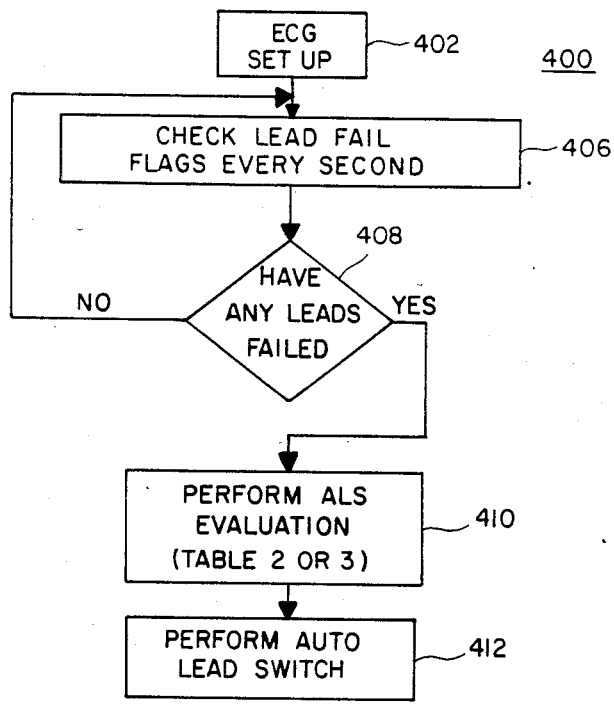
FIG. 4 is a block diagram flow chart of an automatic lead switching portion of the present invention for use by the CPU of FIG. 1.

Referring now to FIG. 4, the automatic lead switching (ALS) 400 is provided by CPU 108 in response to the status of the four bits provided over bus 109 from the comparators 322 through 328. At ECG set up 402 the CPU is informed of the configuration being employed, e.g., by an operator input at interface 112 or automatically by the ECG monitor. If no input is provided a default configuration is assumed, e.g., three lead configuration II.

The CPU periodically checks the lead fail flags from circuit 104. In the preferred embodiment this check is made at least once every second 406. If no leads have failed then the CPU keeps checking once every second 408. However, if only one lead has failed the CPU performs an ALS evaluation 410. This evaluation is described in detail in Table 2 for a five lead cable when a three lead configuration I, II, or III is initially selected, and in Table 3 when a five lead configuration is initially selected. If appropriate an auto lead switch is performed 412.

TABLE 2
AUTO LEAD SWITCH (ALS)
LEAD CONFIGURATIONS I, II, III

| Bad Electrode in Parenthesis | Lead Selected | Auto Lead Switch | Message |
|---|---|---|---|
| (RA) C RL | LA LL | I | III | CHECK LEAD (RA) |
| RA C RL | (LA) LL | I | II | CHECK LEAD (LA) |
| RA C RL | LA (LL) | I | DOES NOT OCCUR | CHECK LEAD (LL) |
| (RA) C RL | LA LL | II | III | CHECK LEAD (RA) |
| RA C RL | (LA) LL | II | DOES NOT OCCUR | CHECK LEAD (LA) |
| RA C RL | LA (LL) | II | I | CHECK LEAD (LL) |
| (RA) C RL | LA LL | III | DOES NOT OCCUR | CHECK LEAD (RA) |
| RA C RL | (LA) LL | III | II | CHECK LEAD (LA) |
| RA C RL | LA (LL) | III | I | CHECK LEAD (LL) |
| RA (C) RL | LA LL | I, II or III | DOES NOT OCCUR | CHECK LEAD (C) |
| RA C (RL) | LA LL | I, II or III | DOES NOT OCCUR | CHECK LEADS |

TABLE 3

| Bad Electrode in Parenthesis | Current Lead monitored | ALS Auto lead switch | Message |
|---|---|---|---|
| AVR, AVL, AVF | | | |
| (RA) C RL | LA LL | AVR, AVL or AVF | III | CHECK LEAD (RA) |
| RA C RL | (LA) LL | AVR, AVL or AVF | II | CHECK LEAD (LA) |
| RA C RL | LA (LL) | AVR, AVL or AVF | I | CHECK LEAD (LL) |
| RA C (RL) | LA LL | AVR, AVL or AVF | DOES NOT OCCUR | CHECK LEADS |
| V LEADS | | | |
| (RA) C RL | LA LL | $V_{1-6}$ | III | CHECK LEAD (RA) |
| RA C RL | (LA) LL | $V_{1-6}$ | II | CHECK LEAD (LA) |

TABLE 3-continued

| Bad Electrode in Parenthesis | Current Lead monitored | ALS Auto lead switch | Message |
|---|---|---|---|
| RA C RL | LA (LL) | $V_{1-6}$ | I | CHECK LEAD (LL) |
| RA C (RL) | LA LL | $V_{1-6}$ | DOES NOT OCCUR | CHECK LEADS |
| RA (C) RL | LA LL | $V_{1-6}$ | II | CHECK LEAD (C) |

For both Tables 2 and 3, based on the existing lead configuration selected (column 2) and the identity of the bad lead detected (the lead shown in parenthesis in column one) the CPU takes the action listed in column 3 and displays the message shown in column 4 on the display 110. Where it is possible to switch to another lead configuration the CPU commands the switch circuit 202 to switch the necessary lead inputs to the analog circuit 204. Where no switch is possible no action besides the display of the message is taken.

For example, in the first row of Table 2, the initial lead configuration is I, i.e. referring to Table 1, the RA signal is subtracted from the LA signal and switch 336 is closed making lead 306, the LL lead, the reference. If a check of the flags shows an unacceptable impedance level for lead 302 (RA) then the CPU switches the leads to configuration III, i.e. LA is subtracted from LL. Switch 336 is opened and switch 332 is closed. A similar discussion can be made for each of the remaining row entries in Table 2.

Tables 2 and 3 were formulated by considering what switching action, if any, could be taken to preserve meaningful ECG measurements for each possible lead configuration/single lead fail combination. In general, when 5 electrodes are attached and the failed lead is not the reference, then a good lead configuration can always be found. The failed lead will result in ALS if the failed lead was necessary for the selected lead configuration (scenario 1) or the failed lead may have no affect on the selected lead configuration and ALS will not be necessary (scenario 2). If the failed lead is the reference, then the monitor believes that *all* leads have failed and another lead cannot be found (scenario 3).

In scenario 1, during the process of looking for another lead, the heart rate calculation is frozen and ECG-/ARR processing is suspended. When the good lead configuration is found, it switches to that configuration and ECG/ARR processing resumes if an acceptable signal is found. (If signal is not acceptable after 6 seconds, an alarm is generated and a message explaining why the signal was not acceptable is displayed in the message line. If the signal becomes acceptable, processing resumes, the tone ceases and the message is extinguished.)

The user is notified of the ALS by two visual indicators: (1) "CHECK LEAD (XX)" message, and (2) flashing of new lead. (There is no audio alarm.) The message goes away and the flashing stops whent he user reattaches the failed electrode IF this is simple to implement.

In scenario 2, if a lead fails that is not necessary for maintaining the selected lead configuration, then the user is notified only by a "CHECK LEAD (XX)" message. (There is no flashing of new lead, and no audio alarm.) The message goes away when the user reattaches the failed electrode IF this is simple to implement.

In scenario 3, during the process of looking for another lead, the heart rate calculation is frozen and ECG-/ARR processing is suspended. When it has been determined that the reference lead has failed, ECG/ARR processing resumes if "R" waves are being detected or processing continues to be suspended if "R" waves cannot be detected. The user is notified that the reference lead has failed by visual and audio indicators.

Multiple lead fail will operate like a reference lead fail (scenario 2).

What is claimed is:

1. An ECG monitor comprising:
   a plurality of ECG leads and associated electrodes for coupling said leads to a patient;
   an ECG signal preprocessor coupled to said leads for combining the signals of said leads in accordance with selected ECG lead configurations chosen from a plurality of possible lead configurations to generate a combined ECG signal, said ECG signal preprocessor further comprising switching means for switching to said selected configurations of ECG leads in response to command signals;
   means coupled to said ECG leads for identifying lead failures continuously during monitoring of said ECG signal; and
   processor means for generating said command signals and coupled to said switching means for automatically switching said leads to change said ECG lead configuration in response to the output of said identifying means.

2. The monitor of claim 1 wherein said identifying means comprises means for determining when the impedance of the electrodes attached to the patient exceeds a predetermined threshold impedance level.

3. The monitor of claim 2 wherein said plurality of leads and associated electrodes comprises:
   a reference lead and associated electrode coupled to electrical ground; and
   wherein said identifying means further comprises:
   a separate dc voltage source of voltage V and series resistor of preselected resistance coupled to each of said leads except said reference lead; and
   a comparator means coupled to the junction of each of said dc voltage sources and series resistors and said leads, said comparator means also coupled to a second dc voltage source having a voltage value less than V by a preselected amount, said comparator means for providing a lead fail output signal when the voltage at the junction drops below said second dc voltage.

4. The ECG monitor of claim 1 wherein said processor means further comprises automatic lead switching means for automatically determining which leads are to be switched to obtain an improved ECG signal in response to the selected lead configuration and the identification of failed leads from said identifying means.

5. The ECG monitor of claim 4 wherein said plurality of lead configurations comprises both three lead and five lead configurations and said automatic lead switching means switches from a selected five lead configuration to a predetermined three lead configuration depending on the output of said identifying means.

6. A method of monitoring a patient's ECG signal formed from a plurality of ECG leads and associated electrodes combined in a selected one of a plurality of possible lead configurations comprising the steps of:
   automatically identifying electrode failures continuously during the monitoring of the patient's ECG signal; and
   automatically changing said selected lead configuration to another lead configuration in response to said identification.

7. The method of claim 6 wherein said method further comprises the step of measuring the impedance offset between each of the active electrodes and a predetermined threshold impedance to determine which electrodes have failed.

8. The method of claim 7 wherein said step of measuring the offset impedance comprises:
   coupling a selected one of said leads and associated electrodes to electrical ground;
   passing a small dc current through each lead and associated electrode and the patient to ground through said selected lead and associated electrode; and
   comparing the dc voltage produced by said dc current with a preselected reference voltage.

* * * * *